US005777035A

United States Patent [19]

Van Dijk et al.

[11] Patent Number: 5,777,035
[45] Date of Patent: Jul. 7, 1998

[54] PROCESS FOR PURIFICATION OF STARTING MATERIALS FOR METAL CATALYZED REACTIONS AND A PURIFICATION REAGENT TO BE USED THEREFOR

[75] Inventors: Cornelis Martinus Van Dijk; Paulus Alexander Maria Grotenhuis; Marc Stephen Sonderman, all of Amsterdam, Netherlands

[73] Assignee: Shell Oil Company, Houston, Tex.

[21] Appl. No.: 882,274

[22] Filed: Jun. 25, 1997

Related U.S. Application Data

[62] Division of Ser. No. 532,121, Sep. 22, 1995, Pat. No. 5,693,726.

[30] Foreign Application Priority Data

Sep. 22, 1994 [EP] European Pat. Off. ............ 94306946

[51] Int. Cl.$^6$ ................................................. C08F 8/42
[52] U.S. Cl. ................................. 525/274; 525/333.4
[58] Field of Search .............................................. 525/274

[56] References Cited

U.S. PATENT DOCUMENTS 3,278,487  10/1966  Kun ............................................. 260/47
3,824,221  7/1974  Ragg .................................... 260/80 PS
4,996,266  2/1991  Bronn et al. ............................. 525/271

FOREIGN PATENT DOCUMENTS

0472749 A1  3/1992  European Pat. Off. .
136503  7/1979  Germany .

OTHER PUBLICATIONS

"Purification of Styrene for Anionic Polymerization" by D. B. Priddy and M. Pirc, *Journal of Applied Polymer Science*, vol. 40, pp. 41–45, John Wiley & Sons, Inc. (1990).

Primary Examiner—Bernard Lipman
Attorney, Agent, or Firm—Donald F. Haas

[57] ABSTRACT

Purifying reagent for the purification of starting materials to be used in a metal compound catalyzed polymerization, containing proton donating reactive contaminants, consisting of a solid product, obtainable by the metallation of a product of a nucleophilic displacement reaction between a halogen alkylated crosslinked poly(vinylaromatic) resin and a metallated conjugated diene compound, which product is insoluble inorganic solvents, which is not able to initiate anionic polymerization of olefins or dienes and which is able to scavenge proton donating contaminants, which may hamper polymerizations catalysted by metal organic compounds; and process for purification of starting materials applying said purifying reagent.

6 Claims, No Drawings

PROCESS FOR PURIFICATION OF STARTING MATERIALS FOR METAL CATALYZED REACTIONS AND A PURIFICATION REAGENT TO BE USED THEREFOR

This is a division, of application Ser. No. 08/532,121, filed Sep. 22, 1995 U.S. Pat. No. 5,693,726.

FIELD OF THE INVENTION

The present invention relates to a process for the purification of starting materials for metal catalyzed reactions and to a purification reagent to be used therefor. More in particular the invention is relating to a process for the purification of starting monomers to be used for a polymerization using a metal containing catalyst, such as an anionic or a Ziegler Natta polymerization.

BACKGROUND OF THE INVENTION

Metal catalyzed reactions are those involving inorganic and organometallic reagents, such as Grignand reagents, alkyllithium reagents, metal halides and metal hydrides, with which reactions proton donating species such as water, alcohols, carboxylic acids, amines, thiols etc, may interfere. Because of the presence of small amounts of water, alcohols or other proton donating species that interfere with many desirable chemical reactions, it may be necessary to purify, i.e. to remove, such contaminants in the starting materials.

Removal of proton donating species from chemical reagents or a chemical reaction system is very important in many reactions involving the hereinbefore mentioned metal containing catalysts. This procedure is especially desirable in the polymerization reactions such as anionic and Ziegler Natta polymerizations.

Reaction mixtures employed in anionic polymerizations are particularly sensitive to contamination and the components should be purified prior to addition of a predetermined amount of an anionic polymerization initiator in order to achieve an accurately reproducible molecular weight product, showing reproducible desired physical properties, a deviation from which may be detrimental for the specifically selected end use applications.

Normally the levels of contaminates in such monomers will vary from batch to batch and it is therefore particularly critical in the manufacture of polymers by means of batch polymerizations to eliminate interfering quantities of contaminates in order to know accurately the actual ratio of still active polymerization initiator to monomer(s). Only in this manner the molecular weight of the resulting polymer may accurately be reproduced from batch to batch.

Techniques for determining the correct amount of purification reagent to be added to a reaction mixture are generally limited to the following procedures.

A small sample of the mixture may be remotely analysed utilising gas chromatography or other suitable analytical techniques to determine the amount of undesirable contaminants occurring therein. Based on said analysis, it is thereafter possible to determine the correct amount of eliminating reagent that should be added to the reaction/mixture.

It will be appreciated that such processes are connected to several deficiencies. Firstly the removal of a sample may itself introduce additional contaminants into the sample. Secondly a sample volume ratio must be employed in the calculation of the amount of purifying reagent which must be added to the reaction mixture, whereby a source or error is introduced. Thirdly, interim variation in the primary solution may develop, while the analysis and calculation are being performed, which causes that a slightly deviating amount of the purifying reagent is added.

An additional technique for determining the correct amount of purifying reagent to be added utilizes titration of the entire reaction mixture utilizing a suitable reagent under conditions such that onset of the reaction with the desirable ingredients in the mixture is detected.

According to one major embodiment of said technique involving anionic polymerization requires the presence of a monomer in the starting polymerization reaction mixture, which may form a clearly colored anionic species. A typical example thereof is a vinyl aromatic monomer such as styrene. The so called titration reagent is in general an alkyllithium and preferably butyllithium initiator used for the actual polymerization initiation. The formation of living polymers will not occur until the substantial elimination of all contaminating species. When this stage is reached, brightly colored polymeric anions will clearly indicate the onset of the polymerization and hence the complete consumption of all contaminating species. It will be appreciated that said indication of the onset of the polymerization will only be applicable to those monomer species, which indeed will form brightly colored anions.

Unfortunately, the conjugated diene monomers which are also applied on large scale as comonomers for the manufacture of elastomeric polymers generally fail to form such brightly colored anions.

Moreover, depending on the position in the spectrum wherein a colored species absorbs and the intensity of that absorption extinction coefficient, a colored end point indication may be of little value. The absorption must occur in an area of the spectrum which is unaffected by other possibly coformed colored species in the reaction mixture and must be of sufficient intensity that extremely small quantities thereof are still detectable.

As indicated earlier, it has been known for a long time to use lower alkyl lithium initiators as titrating reagents. A particular deficiency of the use of such alkyl lithium initiators is the relatively fast reaction of such compounds with the monomers to form polymeric and/or oligomeric species in significant amounts before the complete removal of the contaminants.

More recent efforts to diminish or to eliminate the interference of proton donating contaminants in starting monomers for polymerization reactions are illustrated by e.g. European patent application no. 0472749 and J. Appl. Pol. Sc. 40,41–45 (1990).

The European patent application no. 0 472,749 disclosed a process for purification of a reaction mixture for anionic or Ziegler-Natta polymerization in the polymerization reactor, utilizing a dilithium compound of a specifically selected molecular structure in order to reach rapid reaction with the contaminants and less rapidly with the monomers to be polymerized, while the consumption of contaminants is indicated by a process other than the onset of polymerization. A disadvantage of said process is formed by the fact that an excess of the rather expensive purification reagent is required to ensure complete purification and under certain practical conditions the difunctional lithium compound was found to still initiate anionic polymerization of e.g. monovinylaromatic monomers such as styrene.

The Journal of Applied Polymer Science, Vol. 40 ,p 41–45 (1990) disclosed a purification of styrene monomers for anionic polymerization by reaction with proton donating impurities that interfere with anionic polymerization, by means of using lithium aluminium hydride supported on exchange resin beads derived from polyamine such that the impurity reaction products are chemically bound to the support. In particular polystyrene could be prepared by anionic polymerization in a continuous stirred tank reactor (CSTR).

It will be appreciated that there is still a need for further improved purifying reagents in particular with reference to the recently proposed single solvent/single reactor manufacture of thermoplastic elastomers from monovinyl aromatic and conjugated diene, said purifying reagents not being used within the reaction mixture and avoiding the use of expensive detection methods of the onset of the actual polymerization, i.e. which is not dependent on the formation of colored reaction products such as living polymer anion in an anionically polymerizable mixture. It is therefore an object of the present invention to provide an improved purification process for the removal of contaminants in starting materials for metal compound catalyzed polymerization reactions and in particular, without the formation of polymeric and/or oligomeric species, which process is not dependent on the formation of colored reaction products, such as living polymer anions in an anionically polymerizable mixture, and wherein the purifying reagent reacts rapidly with the impurities in the starting materials and not at all with the monomers to be polymerized under normal reaction conditions and thus avoiding potential runaway of the polymerization reaction.

Another object of the present invention is to provide purifying reagent to be used in such processes. As result of extensive research and experimentation the process and purifying reagent aimed at have surprisingly been found.

SUMMARY OF THE INVENTION

Accordingly the present invention is relating to a purifying reagent for the purification of starting materials to be used in a metal compound catalyzed polymerization, containing proton donating reactive contaminants, the purifying reagent being a solid product obtainable by the metallation of a product of a nucleophilic displacement reaction between a halogen alkylated crosslinked poly(vinylaromatic) resin and a metallated conjugated diene compound.

DETAILED DESCRIPTION OF THE INVENTION

The present invention is a purifying reagent for the purification of starting materials to be used in a metal compound catalyzed polymerization, containing proton donating reactive contaminants, the purifying reagent consisting of a solid product obtainable by the metallation of a product of a nucleophilic displacement reaction between a halogen alkylated crosslinked poly(vinylaromatic) resin and a metallated conjugated diene compound, which product is insoluble in organic solvents, which is not able to initiate anionic polymerization of olefins or dienes and which is able to scavenge proton donating contaminants, which may hamper polymerizations catalysed by metal organic compounds and in particular organolithium anionic polymerization initiators.

With the term "metallated conjugated diene compound" as used throughout this specification, compounds are meant which easily can be covalently bound to the halogen alkylated crosslinked poly(vinylaromatic) resin, acting as support medium, and which can be thereafter easily activated by metallation. Suitable examples of such compounds are metallated cyclopentadiene, which has optionally been substituted by an alkyl having 1 to 6 carbon atoms and preferably from 1 to 3 carbon atoms, an aryl or an aralkyl group, having at most 12 carbon atoms and preferably being phenyl or benzyl. Metallation can be obtained by reaction of a corresponding precursor compound with sodium, potassium or lithium introducing reagents or Grignard reagents.

A preferred group of the metallated conjugated diene compound is formed by lithiated cyclopentadiene, which may be substituted as specified hereinbefore. Most preferably lithium cyclopentadienyl is used.

Another feature of the present invention is relating to a process for the purification of starting materials to be used in a metal compound catalyzed polymerization containing proton donating reactive contaminants, by contacting the starting materials with a purifying reagent obtainable by metallation of the product of a nucleophilic displacement reaction between halogen alkylated crosslinked poly (vinylaromatic) resin and a metallated conjugated diene compound and preferably lithium cyclopentadienyl. The purification process may be performed within a relatively wide range of temperature and/or contact time conditions. Normally the process can be carried out at a temperature from −20° to 90° C. and over a time period from 0.5 minutes to 180 minutes depending on the specific reaction conditions.

The precursor for the purifying reagent to be used according to the present invention can in general be derived from halogenalkylated crosslinked poly(monovinyl aromatic) resin, wherein the halogen alkyl groups may contain from 1 to 4 carbon atoms and preferably 1 or 2. More preferably the halogen atom is chlorine and the most preferred starting component is chloromethylated crosslinked poly(styrene) resin or copolymer of styrene and/or divinylbenzene and methyl styrene and/or o methyl styrene and/or p-methylstyrene and/or dimethyl styrene, such as the commercial product from Aldrich under the tradename "Merrifields" peptide resin.

For the preparation of the precursor of the purifying reagent, e.g. the chloromethylated crosslinked poly(styrene) resin is slurried with a polar organic solvent such as tetrahydrofuran and this solution is added to a solution of e.g. lithium cyclopentadienyl in THF, whereafter the mixture is stirred for 2 hours at a temperature in the range of from 40° to 60° C.

After cooling to ambient temperature, the reaction mixture is filtered and the solids are washed with water to remove the lithium chloride and with methanol to facilitate drying.

After drying at 40° C. under vacuo, e.g. the adduct of cyclopentadiene and crosslinked polystyrene is obtained, having a theoretical cyclopentadiene content of 1.04 meq/g.

Said obtained intermediate precursor has to be metallated into a ready for use product by treatment with a conventional organo metal compound, more preferably lower alkyl lithium compounds and most preferably t-butyllithium or s-butyllithium.

The present purification process may be easily applied on any reaction mixture or the constituting components containing proton donating contaminants.

In the particular case of anionic polymerization of monovinylaromatic and/or conjugated diene monomers and more preferably the polymerization of styrene and/or butadiene or isoprene, the present purification technique may be applied on both monomer and on the solvents.

It will be appreciated that the present purification process shows the following important advantages over the prior art purification processes:

(a) the purifying reagent is insoluble in organic media,
(b) it is easily recyclable,
(c) it does not initiate anionic polymerization of (di)olefins,
(d) it is able to scavenge contaminants which otherwise hamper the polymerization reaction
(e) it may be produced from relatively cheap and simple starting reagents, which are readily available as commercial products.
(f) it is in particular useful for the newly developed manufacturing conception for thermoplastic elastomers derived from monovinyl aromatic and conjugated diene monomers, using a single solvent-single reactor system, in which only a part of the total monomer amount can be titrated, which made this process conception vulnerable towards the presence of impurities in said monomers.

The present purification process is preferably applied in starting materials for anionic polymerizations and more in particular the monovinylaromatic and/or conjugated diene monomer and the organic solvent(s) to be used such as toluene, n-hexane, cyclohexane, n-pentane, isopentane, cyclopentane or mixtures thereof.

Examples of said monomers include styrene, α-methylstyrene, o-methylstyrene, p-methylstyrene, dimethylstyrene and butadiene and/or isoprene or mixtures thereof.

Although a polymerization mixture, comprising the desired reactants e.g. monomers and any diluent or other desired ingredients can be purified according to the present process, according to a preferred embodiment of the process of the present invention the individual components of the polymerization reaction mixture are subjected to purification separately.

More preferably the monomer and/or diluent is led through a column or bed, packed with the purifying reagent, into the actual polymerization reactor. It will be appreciated that such packed bed or column can be reactivated if necessary. This should comprise removal of the monomer via e.g. draining the column, washing the purifying reagent with e.g. methanol, removal of methanol e.g. via a wash with an inert hydrocarbon solvent and subsequently leading through a solution of e.g. s-Butyl lithium in that inert solvent.

On the other hand a mixture of monomers and diluents can be subjected to said purification process by addition of a sufficient amount of purifying reagent in vigorously stirred tank, whereafter the solvent is separated from the purifying reagent in the tank.

Preferred temperatures for conducting the purification process are from −10° to 80° C. and more preferred temperatures are from 0 −70°.

Preferred contact times are in the range of from 2 to 60 minutes. The invention is further elucidated by the following examples, however without restricting its scope to these specific embodiments.

EXAMPLE 1
(a) Preparation of purifying reagent

To a slurry of 20 g chloromethylated crosslinked polystyrene (bought in from Aldrich under the name "Merrifield's peptide resin" with a chlorine content of 3.8% w) in 100 ml THF was added a solution of 3.1 g lithium cyclopentadienyl in 100 ml THF. The mixture was stirred for 2 hours at 50° C. After cooling to ambient, the reaction mixture was filtered.

The solids were washed with water to remove LiCl and with methanol to facilitate drying. After drying at 40° C. under vacuum, 20 g of the adduct of Cyclopentadiene and crosslinked Polystyrene (further to be mentioned CPPS) were obtained. Theoretical cyclopentadiene content amounted to 1.04 meq/g.

To a slurry of 10 g CPPS in 200 ml cyclohexane was added 20 ml of a solution of s-BuLi (0.4M) in cyclohexane. The slurry was stirred at 50° C. for 1 hour. Lithiation of CPPS was indicated by the change in color (from light yellow to dark red) of the solids.

(b) Purification of starting materials from contaminants
After cooling to ambient, 200 ml cyclohexane and 30.8 g styrene were added. The slurry was stirred for 15 minutes to allow scavenging of the contaminants. The complete absence of a red color indicates clearly that CPPSLi is not able to form styryl lithium.

The CPPSLi was then removed from the cyclohexane/styrene mixture by means of a decantation. This yield a clear solution of styrene in cyclohexane. To two 135 g samples was added respectively 3.6 and 2.6 ml s-BuLi in cyclohexane (0.4M). After polymerization at 50° C., the sample was analysed by GPC.

In a blank experiment the above was repeated with the exception of the CPPSLi treatment.

Results of GPC analyses are presented in Table 1 below. The theoretical molecular weight (MnTh) is the molecular weight, which would be obtained if no catalyst killers were present. Mn is the polymer's actual molecular weight.

TABLE 1

| Exp. | CPPSLi treatment | MnTh | Mn | Mn/MnTh |
| --- | --- | --- | --- | --- |
| 1 | yes | 8300 | 8400 | 1.012 |
| 2 | yes | 11500 | 12000 | 1.043 |
| 3 | no | 7100 | 8800 | 1.239 |
| 4 | no | 13800 | 18400 | 1.333 |

The results clearly demonstrate the scavenging ability of CPPSLi.

We claim:
1. A purifying reagent for the purification of starting materials to be used in a metal compound catalyzed polymerization, the reagent consisting of:

a solid product produced by a process of metallating a product of a nucleophilic displacement reaction between a halogen alkylated crosslinked poly (vinylaromatic) resin and a metallated conjugated diene compound, which product is insoluble in organic solvents, is not able to initiate anionic polymerization of olefins or dienes, and is able to scavenge proton donating contaminants.

2. The purifying reagent according to claim 1, wherein the solid product is produced by metallating a product of a nucleophilic displacement reaction between a halogen alkylated crosslinked poly(vinylaromatic) resin and a metallated cyclopentadiene, which has optionally been substituted by an alkyl having 1 to 6 carbon atoms, or an aryl or an aralkyl group having at most 12 carbon atoms.

3. The purifying reagent according to claim 1, wherein the solid product is produced by metallating a product of a nucleophilic displacement reaction between a halogen alkylated crosslinked poly(vinyl aromatic) resin and a lithium cyclopentadienyl.

4. The purifying reagent according to claim 1, wherein the solid product is produced by metallating a product of a nucleophilic displacement reaction between a chloroalkylated crosslinked poly(styrene) or crosslinked copolymer of styrene and one or more compounds selected from a group consisting of α-methyl styrene, o-methylstyrene, p-methylstyrene, dimethylstyrene, and divinylbenzene.

5. The purifying reagent according to claim 4, wherein the solid product is produced from the chloroalkylated crosslinked poly(styrene).

6. The purifying reagent according to claim 1, wherein the metallated conjugated diene compound is t-butyllithium or s-butyl lithium.

* * * * *